United States Patent
Kahn et al.

(10) Patent No.: US 10,424,183 B1
(45) Date of Patent: Sep. 24, 2019

(54) SMART SEATING SYSTEM

(71) Applicants: Philippe Richard Kahn, Santa Cruz, CA (US); Arthur Kinsolving, Santa Cruz, CA (US); Mark Andrew Christensen, Santa Cruz, CA (US)

(72) Inventors: Philippe Richard Kahn, Santa Cruz, CA (US); Arthur Kinsolving, Santa Cruz, CA (US); Mark Andrew Christensen, Santa Cruz, CA (US)

(73) Assignee: DP TECHNOLOGIES, INC., Scotts Valley, CA (US)

( * ) Notice: Subject to any disclaimer, the term of this patent is extended or adjusted under 35 U.S.C. 154(b) by 0 days.

(21) Appl. No.: 15/877,316

(22) Filed: Jan. 22, 2018

Related U.S. Application Data (60) Provisional application No. 62/448,408, filed on Jan. 20, 2017.

(51) Int. Cl.
*A61B 5/05* (2006.01)
*G08B 21/24* (2006.01)
*A47C 7/62* (2006.01)
*A61B 5/0205* (2006.01)
*A61B 5/11* (2006.01)

(52) U.S. Cl.
CPC .............. *G08B 21/24* (2013.01); *A47C 7/62* (2013.01); *A61B 5/0205* (2013.01); *A61B 5/1118* (2013.01)

(58) Field of Classification Search
CPC ......... G08B 21/24; A47C 7/62; A61B 5/1118; A61B 5/0205
See application file for complete search history.

(56) References Cited

U.S. PATENT DOCUMENTS

| | | | | |
|---|---|---|---|---|
| 2002/0193707 A1* | 12/2002 | Atlas | ................... | A61B 5/0205 600/595 |
| 2007/0072156 A1* | 3/2007 | Kaufman | ............... | G16H 20/60 434/236 |
| 2008/0171914 A1* | 7/2008 | Ouwerkerk | .............. | A61B 5/16 600/300 |
| 2010/0049278 A1* | 2/2010 | Kuramori | ............ | A61B 5/0488 607/48 |
| 2012/0290215 A1* | 11/2012 | Adler | ..................... | G16H 50/30 702/19 |
| 2016/0192874 A1* | 7/2016 | Canavan | ............ | A63B 24/0062 600/595 |
| 2017/0092094 A1* | 3/2017 | Yang | .................. | G08B 21/0415 |

* cited by examiner

*Primary Examiner* — Munear T Akki
(74) *Attorney, Agent, or Firm* — HIPLegal LLP; Judith Szepesi (57) ABSTRACT

A smart seating system is described. In one embodiment, the smart seating system may be integrated into a chair or seat, or may be a cushion that is placed on a seat. In one embodiment, the smart seating system uses one or more sensors to monitor the user. In one embodiment, the sensors may be sufficiently sensitive to monitor the user's respiration and heart rate, as well as whether the user is sitting or not. In one embodiment, the smart seating system can be used to monitor a user's breathing and heart rate. The system may be used to control stress in an office environment, in one embodiment. In addition to controlling stress, the smart seating system may be used to coach users to more healthful behaviors.

20 Claims, 9 Drawing Sheets

SMART SEATING SYSTEM

RELATED APPLICATION

The present application claims priority to U.S. Provisional Application No. 62/448,408, filed on Jan. 20, 2017, and incorporates that application in its entirety.

FIELD

The present invention relates to seating, and more particular to a smart seating system.

BACKGROUND

Most adults and children spend much of their day sitting at a desk or in a car. Excessive sitting is not healthy. There are a number of computer applications that attempt to encourage office workers, and students, to move on a regular basis. For example, applications that run a timer on the user's computer, and prompt the user to get up and move around after a certain amount of time.

BRIEF DESCRIPTION OF THE FIGURES

The present invention is illustrated by way of example, and not by way of limitation, in the figures of the accompanying drawings and in which like reference numerals refer to similar elements and in which.

DETAILED DESCRIPTION

A smart seating system is described. The smart seating system may be integrated into a chair or seat, or may be a cushion or cover that is placed on a seat. In one embodiment, the smart seating system uses one or more sensors to monitor the user. In one embodiment, the sensors may be sufficiently sensitive to monitor the user's respiration and heart rate, as well as whether the user is sitting or not. In one embodiment, the smart seating system can be used to monitor and coach users to control their breathing and heart rate to control stress in an office environment. In addition to controlling stress, the smart seating system may be used to coach users to more healthful behaviors.

The following detailed description of embodiments of the invention makes reference to the accompanying drawings in which like references indicate similar elements, showing by way of illustration specific embodiments of practicing the invention. Description of these embodiments is in sufficient detail to enable those skilled in the art to practice the invention. One skilled in the art understands that other embodiments may be utilized and that logical, mechanical, electrical, functional and other changes may be made without departing from the scope of the present invention. The following detailed description is, therefore, not to be taken in a limiting sense, and the scope of the present invention is defined only by the appended claims.

Figure 1:
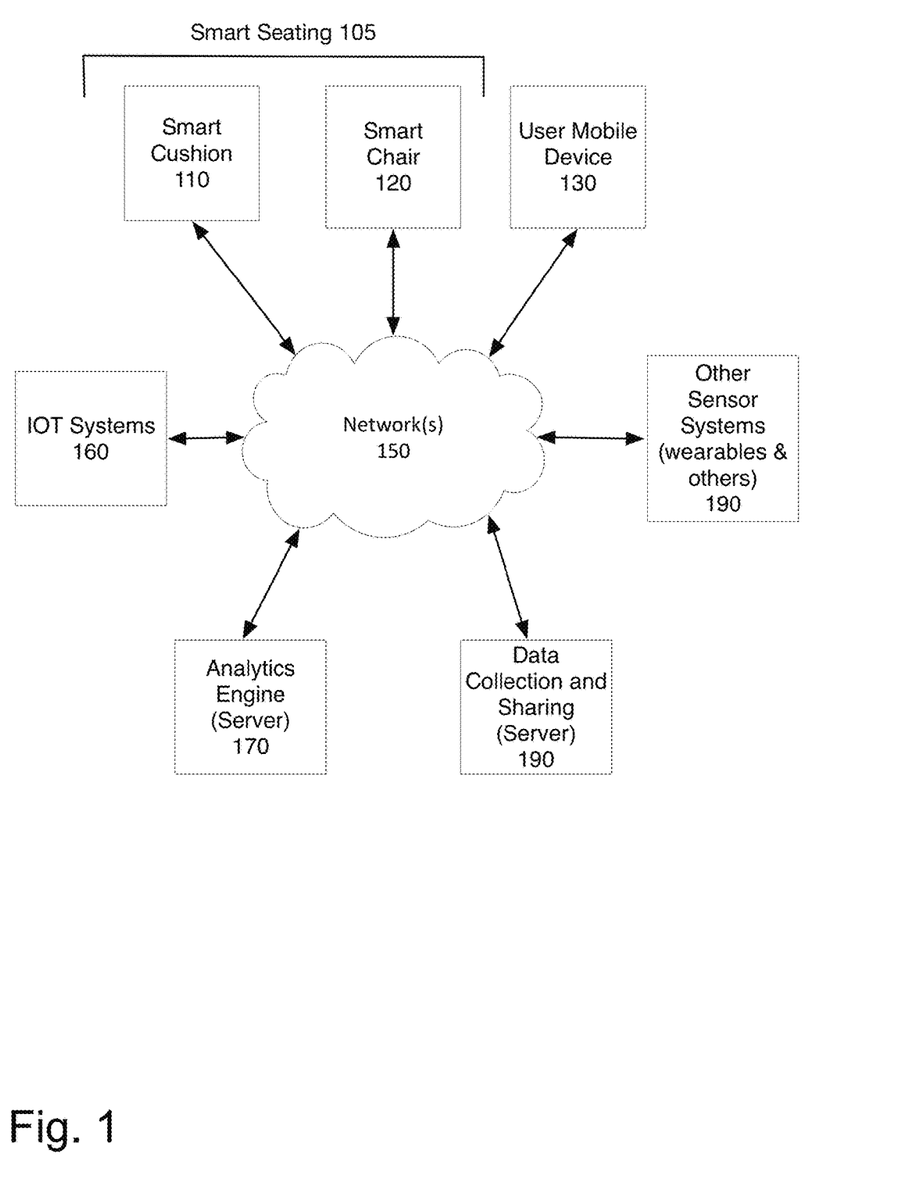
FIG. 1 is a network diagram of one embodiment of a network in which the smart seating system may be implemented.

FIG. 1 is a network diagram of one embodiment of a network in which the smart seating system may be implemented. The smart seating system may include a smart cushion 110 and/or smart chair 120, and a user mobile device 130. The user mobile device 130 is used to collect data from the smart seating 105, which includes a smart cushion 110 and/or smart chair 120, in one embodiment. In another embodiment, the smart seating 105 may include a direct network connection, rather than connecting via a mobile device 130. In one embodiment, the smart seating 105 and/or mobile device 130 may be used to interact with an Internet of Things (IOT) system 160. The IoT system 160 may provide voice control, music, and other options. The IOT system 160 may also be used to control the user's environment.

In one embodiment, the smart seating 105 and mobile device 130 may also interact with other sensor systems 190, which collect data from the user. These other sensor systems 190 may include wearable devices—such as smart watches, wristbands, chest straps, ear buds, or other wearable sensors—as well as other sensor systems such as in-bed systems, medical monitoring systems. User mobile device 130 may also be considered another sensor system, since it too can provide monitoring data about the user. In this context, the user mobile device 130 encompasses a smart phone, a smart headset, glasses or other systems that portably provide network connection and processing power, and may include one or more sensors.

In one embodiment, data from the smart seating 105, other sensor systems 190, and user mobile device 130 may be used by analytics engine on server 170 to make recommendations to the user. Such recommendations may include, for example, times to stretch or be more active, time to rest, etc. In one embodiment, data collection and sharing server 180 collects cumulative data from users, and utilizes the cumulative data to make recommendations. In one embodiment, cumulative data from large numbers of users may also be used as a basis for health analytics for the community and individual users.

Figure 2:
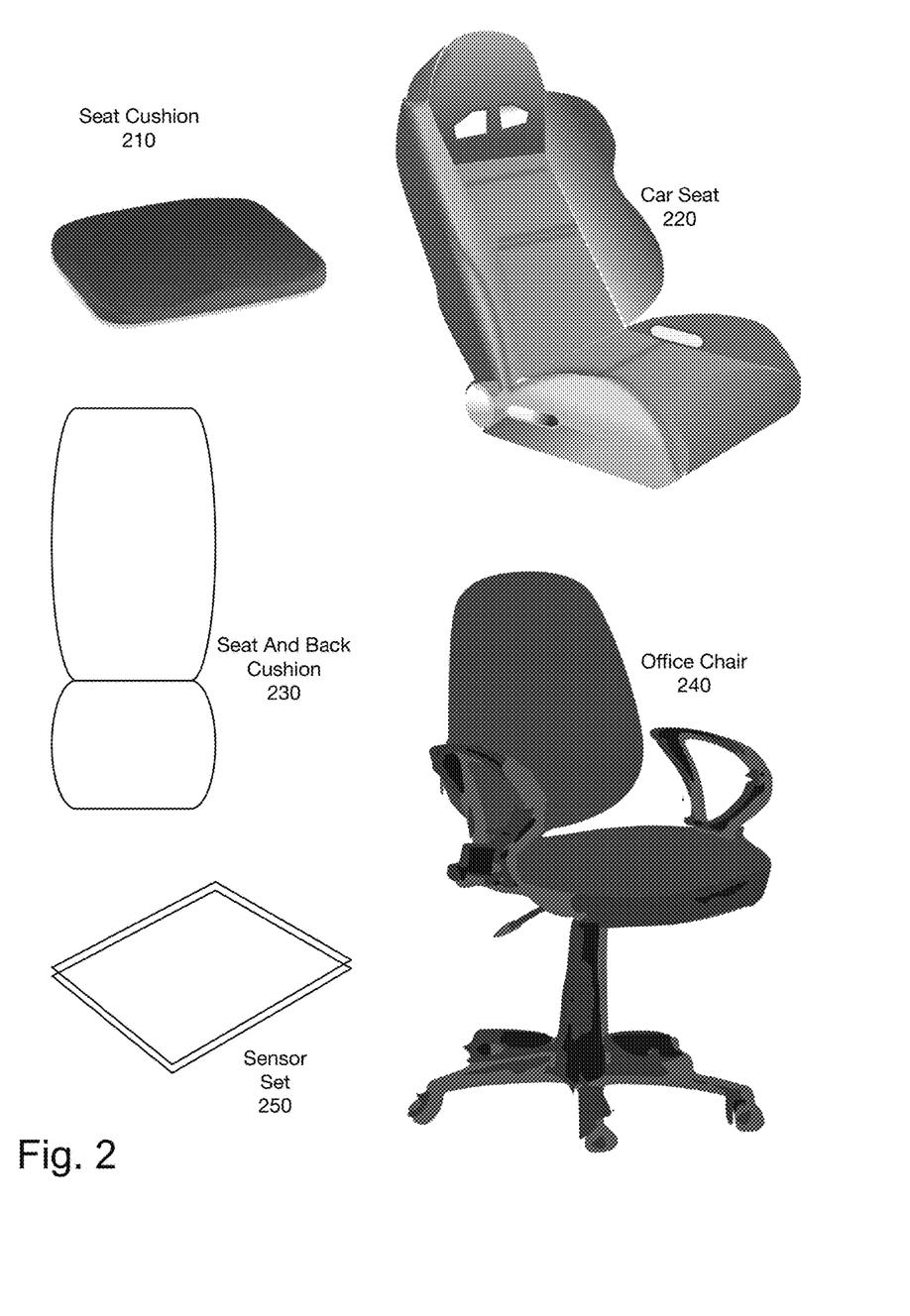
FIG. 2 illustrates some exemplary configurations for the smart seating, which is part of the smart seating system.

FIG. 2 illustrates some exemplary configurations for the smart seating, which is part of the smart seating system. The smart seating is a special purpose device, designed to provide real-time sensor data and feedback to a user. The smart seating may comprise a seat cushion 210, or seat and back cushion 230. Though the term "cushion" is used the surface need not have significant cushioning. The smart seating system has sufficient cushioning incorporated so that the user cannot feel the sensor, to ensure comfort. Such cushions are portable and may be taken by a user to any location. This is advantageous because it enables the smart seating functionality to be portable.

Alternatively, the smart seating may be integrated into a car seat 220 and/or office chair 240. In one embodiment, if the smart seating is incorporated into a car seat 220, the smart seating may be directly powered through a vehicle. This may enable the smart seating to provide analytics and processing functionality, by integrating a processor.

Other configurations of smart seating may be utilized. For example, a stool or other configuration of seating may have an integrated smart seating feature. Additionally, and alternatively, contoured cushions such as those recommended for individuals with back problems may provide smart seating functionality. In one embodiment, the smart seating may include a flat sensor set 250, which is designed to be slid underneath a cushion or on the floor underneath a chair. In one embodiment, sensor set 250 may be integrated into a floor mat, designed to be placed under a chair. In such an embodiment, the sensor set 250 may be able to monitor the user while standing on the mat, as well as while seated. Other configurations of the smart seating may be utilized. The special purpose device of the smart seating system provides monitoring based on motion sensing, in one embodiment.

Figure 3:
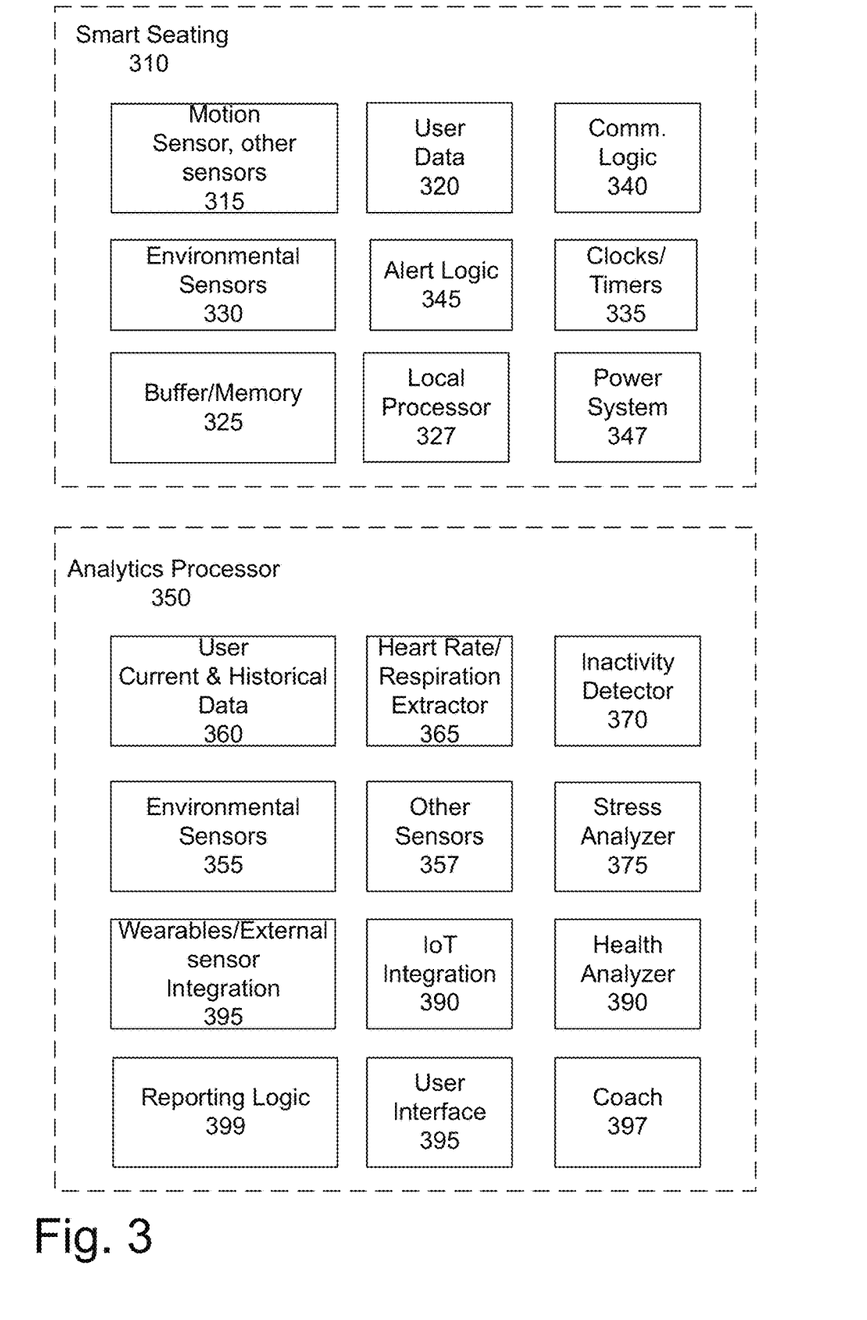
FIG. 3 is a block diagram of one embodiment of the smart seating system including smart seating and an analytics processor.

FIG. 3 is a block diagram of one embodiment of the smart seating system including smart seating and an analytics processor. Note that the analytics processor 350 functionality may be provided by the user mobile device, by the smart seating itself, and/or by the analytics server, or a combination of these elements.

Smart seating 310 includes in one embodiment motion sensors and other sensors 315. In one embodiment, the motion sensor is a pressure-based sensor. In one embodiment, the motion sensor is a LDC1000, LDC1612, or LDC1614 inductor sensor system from TEXAS INSTRUMENTS® is used as the inductive sensor. Other sensors may include gyroscopic sensors, proximity sensors, and temperature sensors. In one embodiment, other sensors may also be used.

User data 320 is sensor data collected from the motion sensor 315. Buffer/memory 325 stores data locally, in one embodiment. In one embodiment, buffer/memory 325 is a FIFO buffer, which can store a limited amount of data. In one embodiment, local processor 327 may process the data before storing it in memory 325. In one embodiment, the processor 327 pre-processes the data to reduce the data volume. In another embodiment, some or all of the functionality of the analytics processor may be executed on the smart seating 310.

In one embodiment, communication logic 340 sends the data to analytics processor. In one embodiment, communication logic 340 may utilize low-power Bluetooth (BLE) for a continuous connection. In another embodiment, communication logic 340 may be a bus providing data to a local analytics processor in one embodiment, communication logic 340 may also receive data from analytics processor. In one embodiment, alert logic 345 enables a tactile alert for the user, such as a vibration. This may be useful to alert the user to move, shift, stretch or otherwise change behavior.

In one embodiment, smart seating 310 may also include environmental sensors. Such sensors may include space temperature sensors, air quality sensors, and other sensors which are not sensing the user's own circumstances but rather the user's environment. In one embodiment, while these sensors are shown as part of smart seating 310 they may be external sensors.

In one embodiment, smart seating 310 includes clocks/timers 335. In one embodiment, an internal clock may be used to set the periodic measurements, power management, and control other aspects of the smart seating 310. In one embodiment, a user clock may be used to time the user, and trigger user notifications. This enables smart seating 310, in one embodiment, to alert the user to move, stretch, or otherwise change their activity periodically even if the analytics processor 350 is not available. In one embodiment, alert logic 345 may alert the user periodically to move. It is well known, physiologically, that it is unhealthy to stay seated too long, without getting up to stretch. Especially when a user is engaged in repetitive activity, such as typing, periodically focusing elsewhere and getting up is important for health. In one embodiment, smart seating 310 may be able to provide such alerts. In one embodiment, the smart seating 310 may detect repetitive activity such as typing, as well as detecting lack of activity such as watching a video, reading, or sleeping. Repetitive activity, in one embodiment, may be treated differently than lack of activity, as will be described in more detail below.

In one embodiment, smart seating 310 includes power system 347. Power system 347 in one embodiment, comprises a wired connection to a power outlet. In another embodiment, the power system 347 comprises batteries and power management. In one embodiment, power management ensures that the sensors are only active when the smart seating 310 is in use. In one embodiment, a simple proximity sensor or similar low power consuming sensor is used, and the power system 347 selectively turns on the other elements of the system when the smart seating 310 is in use. In one embodiment, the power system 347 may include wireless charging, wired charging of a rechargeable battery. In another embodiment, the power system 347 may rely on replaceable batteries. In one embodiment, the smart seating 310 may be made available with a combination of these power system 347 options.

Analytics processor 350 in one embodiment is implemented as a distributed processor over at least two of a local processor in the smart seating 310, a local computer system such as the user's mobile device, and a remote analytics server. In one embodiment, the analytics processor 350 may be a cloud-based system. In one embodiment, the local processing may provide preliminary processing of data, and time-based alerts and actions, while the analytics processor may provide historical data analysis, group data analysis, and recommendations.

In one embodiment, the analytics processor 350 collects user current and historical data 360. This data may be received from the smart seating 310 as well as other sensor systems, as discussed above.

In one embodiment, the analytics processor 350 may include environmental sensors 355. As noted above, the environmental sensors may be provided by the user mobile device or other sensor systems. It may monitor the user's environment including air quality, temperature, lighting, etc. In one embodiment, analytics processor 350 includes wearables/external sensor integration 385, which integrates data from the smart seating 310 and other sensors 357. In one embodiment, the integrated data is stored a user current & historical data. In one embodiment, the system merges the data from the plurality of different sources in different formats into a data stream to enable a better functioning of the analytics processor 350.

In one embodiment, sensor data is analyzed to extract heart rate and respiration, by extractor 365. In one embodiment, extractor 365 utilizes the motion data of the user to determine the heart rate and respiration. In one embodiment, a ballistocardiogram is used to detect heart rate based on the motion data. Of course, the user data also reflects when the user is seated.

In one embodiment, inactivity detector 370 detects when the user has not moved from the seat in a period of time. In one embodiment, the period may be set by default, for example recommending movement every 30 minutes. In one embodiment, the recommendation may also vary based on the detected activity of the user. For example, if a user is watching videos, alerting the user to move every 30 minutes would likely be useful. If the user is typing rapidly, taking a short stretch break every 15 minutes may be more productive. In one embodiment, the user may adjust the recommendations, based on his or her preferences. In one embodiment, the period may be customized for the user, based on the user's real data. Some people do better with shorter periods between breaks, and some do better with longer focus times. In one embodiment, the user may provide user feedback through user interface 395. In one embodiment, the system provides a recommendation customized for the user. The user may adjust the recommendation by some percentage, in one embodiment up to 50%. So, if the user recommended alerts are to move ever 30 minutes, the user may adjust that between 15 minutes and 45 minutes. Other periods may be used.

Stress analyzer 375 analyzes the user's stress level based on motion data, and heart rate data, as well as user input optionally. In one embodiment, the stress level is defined based on a baseline heart rate identified for the user, the user's current heartrate, and the user's motion data. The characteristic pattern of stress is dependent on the individual user. However, generally a decrease in the parasympathetic influences on the heart rate and an activation of the humoral—metabolic and sympathetic influences is identified. Additionally, the breathing becomes shallower and more rapid without concomitant exercise or other cause for the change in the pattern. The stress analyzer 375 may be used to adjust alerts to the user, as well as recommendations for breaks, meditation, or exercise for stress reduction.

Health analyzer 380 may be used to detect other health problems based on analysis of the user's data from the sensors. In one embodiment, for example, a stroke can be detected based on an uneven position in seating (someone having a stroke leans strongly to one side), and a heart attack or heart arrhythmia can be detected based on the ballistocardiogram data. In one embodiment, the system may provide a user interface 395 to alert the user, and optionally third parties if such health issues are detected.

In one embodiment, coach 397 may be used to provide relaxation and focus exercises to the user. In one embodiment, coach 397 may provide periodic relaxation, stretching, or activities. In one embodiment, coach 397 may interact with user through an IoT device, mobile device, or the user's computer. In one embodiment, coach 397 may simply provide an alert to prompt the user to move from inactivity, or do stress reduction exercises. In another embodiment, coach 397 may provide guided meditation or stress reduction, stretching or other exercises. In one embodiment, the user may set his or her preferences for coaching. In one embodiment, the user's compliance and results from prior interactions may adjust the type of coaching provided by coach 397.

In one embodiment, the analytics processor 350 may also provide IoT integration 390. IoT integration 390 may provide additional input/output mechanisms such as voice control, adjustments of the environment (e.g. adjusting heating/cooling, light levels, light tones, fans or other air quality, etc.)

Reporting logic 399 provides to the user a cumulative data set of the user's behavior. In one embodiment, reporting logic 399 may provide integrated data from the smart seating 310 and other sensors 357, as well as reporting of how the user reacted to coaching, and other relevant data. In one embodiment, reporting logic 399 may provide individual and/or cumulative reports to other relevant parties. For example, the smart seating system may be part of a corporate wellness system which reports on users committing to and doing stretches, meditation, and following other healthful behaviors. Such data may be provided, with privacy safeguards, to employers or other relevant parties. In one embodiment, reporting logic 399 may also provide reports to the user's health practitioners. This may be useful to provide a baseline to a medical professional, as well as potentially to identify a start of a health condition based on changes in user health and behavior over time.

In this way, smart seating 310 may become part of an integrated health system. Because many office workers spend most of their day sitting, having a smart seating system 310 as part of an integrated monitoring system provides advantages over traditional monitoring. Additionally, by integrating data from a plurality of sensors which come in and out of contact with the user, the integrated monitoring system can improve the functioning of physiological monitoring technologies. This improvement to the monitoring systems and technologies in the market is the target of the present application.

Figure 4:
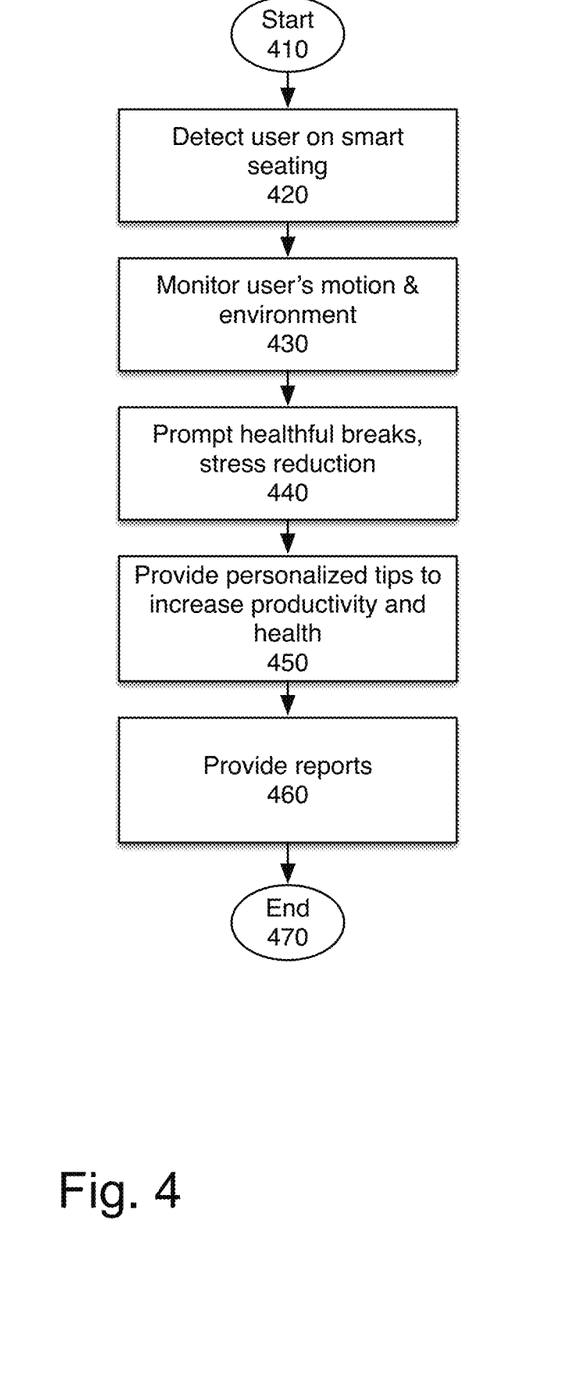
FIG. 4 is an overview flowchart of one embodiment of using the smart seating system.

FIG. 4 is an overview flowchart of one embodiment of using the smart seating system. The process starts at block 410. At block 420, the user is detected on the smart seating. In one embodiment, there may be a simple sensor which detects the user being on the smart seating. The sensor may be a motion, weight, or proximity sensor, for example. In one embodiment, the sensor monitoring is enabled when the user is detected on the smart seating.

At block 430, the user's motion and environment are monitored using one or more sensors.

At block 440, healthful breaks and stress reduction are prompted. In one embodiment, this prompting is based on a combination of the user's activity (or inactivity), repetitive activity, specific activity type, and detected stress level. In one embodiment, based on a combination of these factors the user is prompted to stretch, take a break, walk around or do some exercises, when appropriate.

At block 450, the system provides personalized tips to increase productivity and health. These tips may include suggestions on what to do during work (e.g. take more frequent breaks for stretching) as well as suggestions for what to do outside work (e.g. get at least 7 hours of good quality sleep). Other suggestions may include meditation routines, and other recommendations that would assist the user. In one embodiment, these recommendations are based on current medical research and the user's own data from the smart seating and other sensors.

At block 460 reports are provided. In one embodiment, the reports are made available to the user. Additionally, reports may be made available to third parties. The process then ends, at block 470. In one embodiment, the process stops when the user is no longer on the smart seating. In one embodiment, reports are made available after a short period, when sufficient data is available to show to the user. These reports may be available at any time.

Of course, though this and other processes are shown as flowcharts, the ordering of the steps may vary, and steps may be skipped or repeated, as appropriate.

Figure 5:
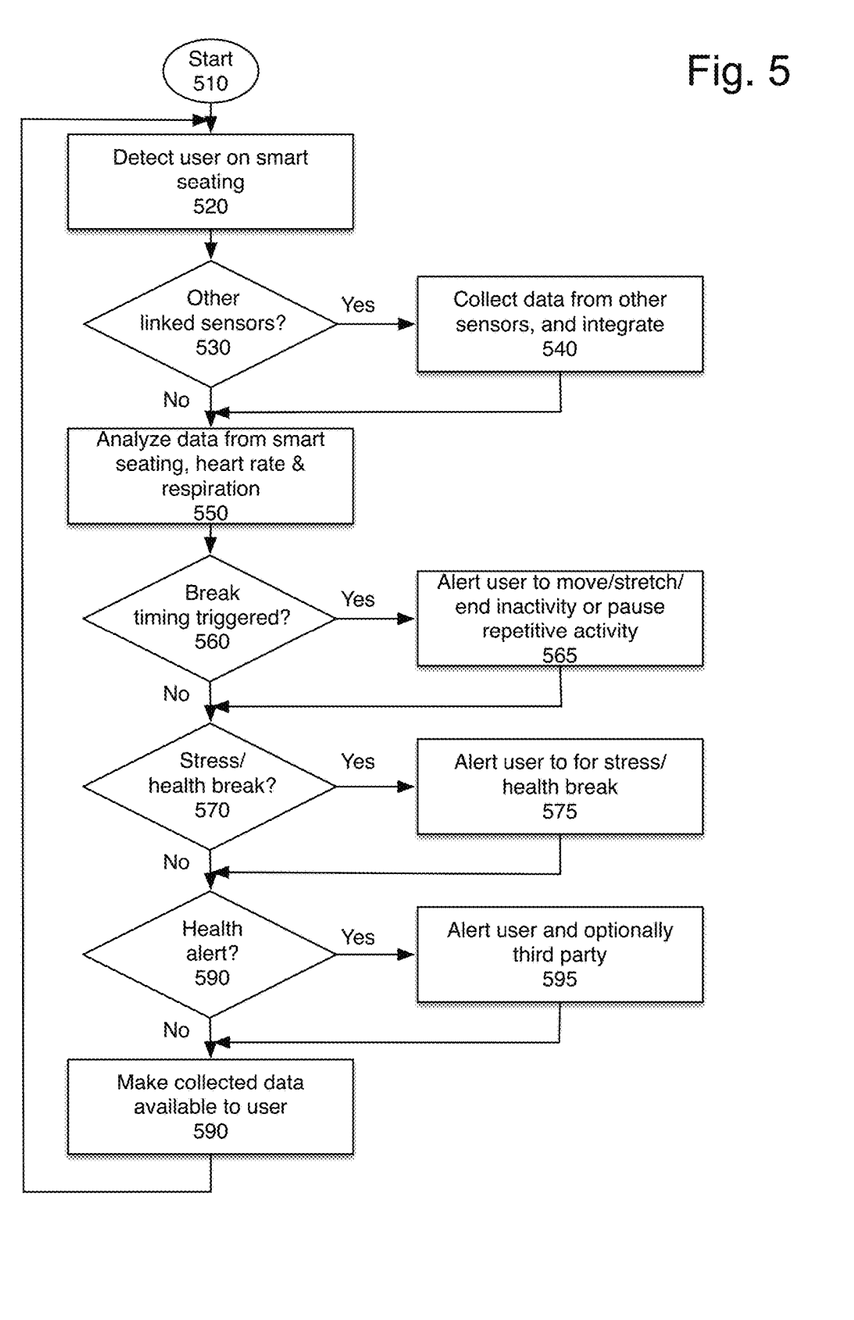
FIG. 5 is a flowchart of one embodiment of utilizing the smart seating system for recommendations.

FIG. 5 is a flowchart of one embodiment of utilizing the smart seating system for recommendations. The process starts at block 510. At block 520 the process detects the user on the smart seating. As noted above, this indicates that the user is at their seat, or the cushion is in use.

At block 530, the process determines whether there are other sensors being used. Other sensors may include sensors in wearable devices being worn by the user, in the user's mobile phone or other device etc. If data is available from other sensors, at block 540 that data is collected.

At block 550, the data from the smart seating and optionally the other sensors are integrated and analyzed. Integration obtains time stamped data from a plurality of sources and integrates it into a complete data set. This complete data set is analyzed. The analysis, in one embodiment, extracts the heart rate and respiration for the user. The heart rate in one embodiment includes the beats per minute (BPM) and the variability and the consistency of the heart rate. The respiration in one embodiment includes the frequency, length, and depth of the respiration. Other data, such as micromotions may also be used.

At block 560, the process determines whether the break timing is triggered. In one embodiment, after a period of inactivity the user is prompted to move. In one embodiment, after a period of repetitive motion, such as typing, the user is prompted to move. The period of inactivity may be of a different duration than the period of repetitive motion for triggering a prompt. In one embodiment, because the smart seating system monitors real movement, the system can differentiate between true inactivity (e.g. lack of body movement) and limited activity (e.g. activity without getting up.) Limited activity for example may involve filing documents, having an in-person conversation with gestures, or other seated activity which include some non-repetitive movement. Contrast that with immobility such as watching TV without interaction. If the break timing is triggered, at block 565 the user is alerted to move, stretch, and end the inactivity or take a break in the repetitive activity. In one embodiment, the system may provide specific coaching for the type of stretches or movements to do for optimal health, alertness, and effectiveness at work or play.

In one embodiment, the stretches or movements may also be based on the user's integrated monitoring system data. For example, a user who has been inactive for the whole day may have a different recommendation for moving (e.g. walk around the block rapidly) than another use who has completed a workout and is now inactive (get up and stretch). In one embodiment, by integrating data from a variety of available sensors the integrated monitoring system is improved.

At block 570, the process determines whether the user should take a health/stress break. In one embodiment, a health/stress break is recommended when the system determines that the user's stress level is above a threshold. In one embodiment, a health/stress break is recommended periodically regardless of the stress level detected based on respiration and heart rate. In one embodiment, the health/stress break is recommended at least once a day, and more frequently for users who are stressed, or for users who are having other health issues. For example, if the integrated data from other sensors such as sleep sensors in the user's bed provide data indicating that the user has insomnia, the system may adjust the stress/health breaks to improve the user's sleep.

At block 575, the user is alerted for a stress/health break. In one embodiment, a stress/health break may include one or more of guided meditation, unguided meditation, instructions to take a walk or go outside, and similar recommendations for actions which are known to reduce stress level and increase healthfulness.

At block 580, the process determines whether the data indicates the need for a health alert. A health alert is generally something more serious than stress, such as heart arrhythmia, potential stroke, or other significant health condition. If a potential health condition is detected, at block 585 the user and optionally a relevant third party is alerted. The third party may be a supervisor in a work environment, a spouse or parent or sibling in a family environment, and a medical professional or emergency health service in some circumstances.

At block 590 the collected data from the smart seating and optionally other integrated sensors are made available to the user. The user may, based on this data, input user preferences. For example, the user may determine that he or she feels better after a certain kind of guided meditation. These types of preferences and user emotional reactions may be input through a user interface and used to adjust the system's recommendations and timings. The process then returns to block 520 to continue collecting data through the system.

Figure 6:
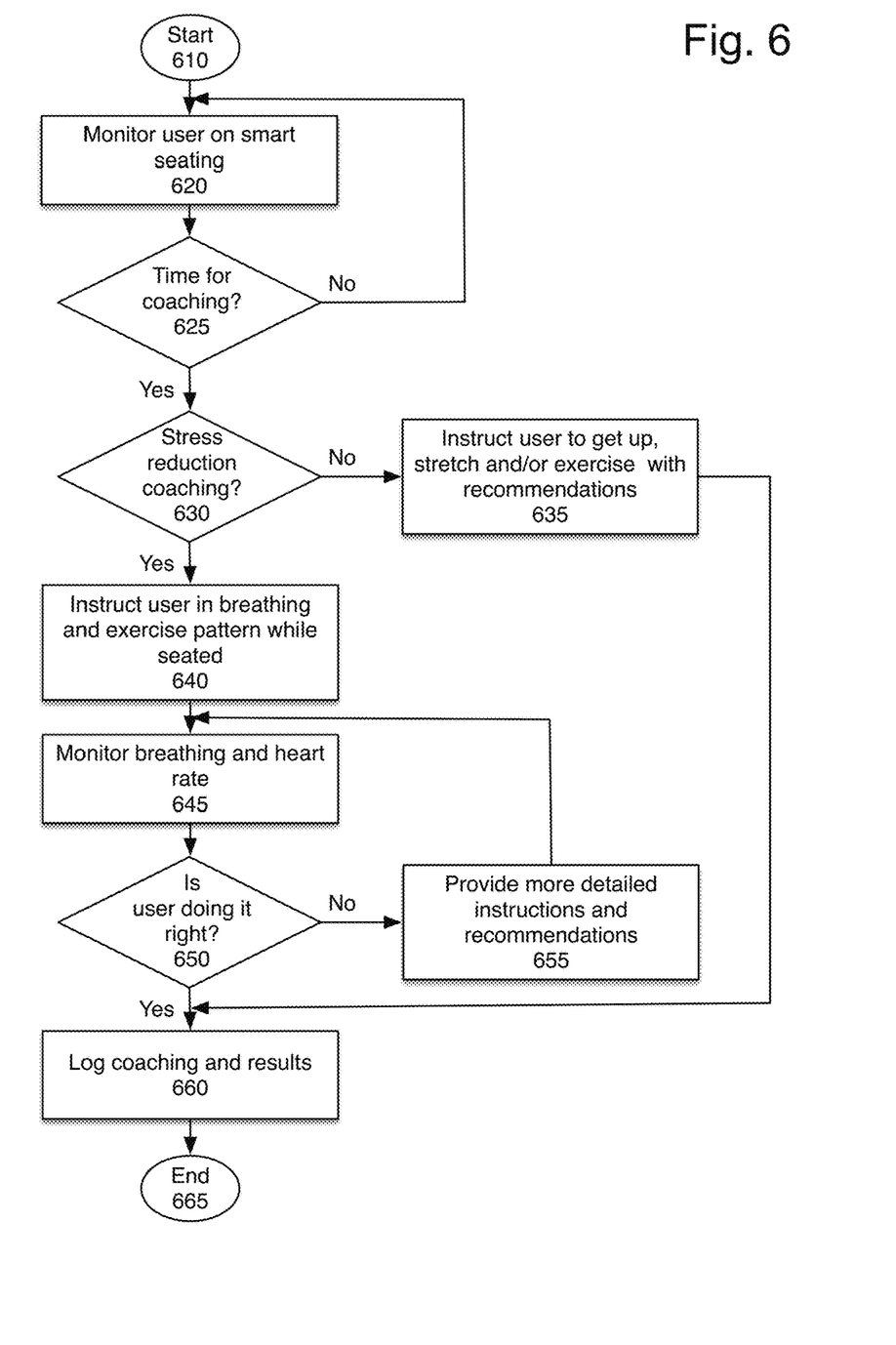
FIG. 6 is a flowchart of one embodiment of utilizing the smart seating system for smart coaching.

FIG. 6 is a flowchart of one embodiment of utilizing the smart seating system for smart coaching. The process starts at block 610. In one embodiment, this process corresponds to blocks 570 and 575 of FIG. 5.

At block 620, the user is monitored on the smart seating. At block 625 the process determines whether it's time for coaching. If not, the process continues to monitor at block 620. If it's time for coaching, the process continues to block 630.

At block 630, the process determines whether the coaching is stress-reduction coaching. If not, then the coaching is for health coaching, and the user is instructed to get up and stretch and/or exercise. In one embodiment, the system provides specific recommendations (e.g. go outside and take a 10-minute walk, or perform the following set of stretches to reduce the risk of carpal tunnel syndrome, etc.)

The process then continues to block 660, to log the coaching and results. In one embodiment, the coaching results may include the user's body reactions after coaching (e.g. reduced heart rate, deeper respiration), the user's emotional reactions (e.g. the user indicates that he or she feels better), and the user's compliance (e.g. whether the user did the stretches or took the walk as instructed.) In one embodiment, the coaching periodically asks the user for his or her emotional reactions. The process then ends at block 665.

Because the system accumulates data about the user, the system can adjust the recommendations based on what is effective. Additionally, the system can adjust the recommendations based on the user's actions after receiving a recommendation. In one embodiment, the system monitors whether the user takes a break after an alert. Cumulatively this will build up a profile of the user's behaviors and reactions to alerts and information provided. In one embodiment, the system may provide A/B testing of various types of alerts, varying the timing, format, insistence, and reminder timing for an alert. This enhances the system's effectiveness as a unified monitoring system.

If the coaching, as evaluated at block 630, was for stress reduction, the process continues to block 640.

At block 640, the process provides instructions for the user for seated exercises. These seated exercises may include specific guided meditations, deep breathing exercises, and other types of exercises. In one embodiment, the exercises may include music or tones played by the user's mobile device, to assist in this, as well as verbal coaching optionally.

At block 645, the breathing and heart rate are monitored.

At block 650, the process determines whether the user is doing it right, e.g. whether the coaching is having its intended effect. In one embodiment, the intended effect is to deepen breathing and slow down the heart rate, as this is shown to correlate with reducing stress. If the user is doing it right, the coaching session is completed. The process then logs coaching and results at block 660. If the user is not doing it right, or it is not having the desired effect, at block 655 more detailed instructions and recommendations are provided. In one embodiment, this may include varying the music/sounds, providing different instructions on how to meditate or otherwise varying the process to increase effectiveness. The process then returns to block 645 to continue monitoring the user's breathing and heart rate with the altered guidance. In one embodiment, the system may attempt a limited set of meditation guidance approaches, such as focused attention meditation, Zen meditation, mindfulness meditation, mantra meditation, and other forms of meditation. In one embodiment, the system adjusts the set of meditations attempted until a form that works well for the user is identified. In one embodiment, the set of meditations chosen may be based on statistical data from a large pool of users by selecting the type of meditation that is most likely to work for a user of this type. In one embodiment, the user type may be identified based on user characteristics (e.g. age, gender, occupation), circumstances (e.g. current health and stress levels), location, and other factors.

In this way, the user's health and wellness is improved.

Figure 7:
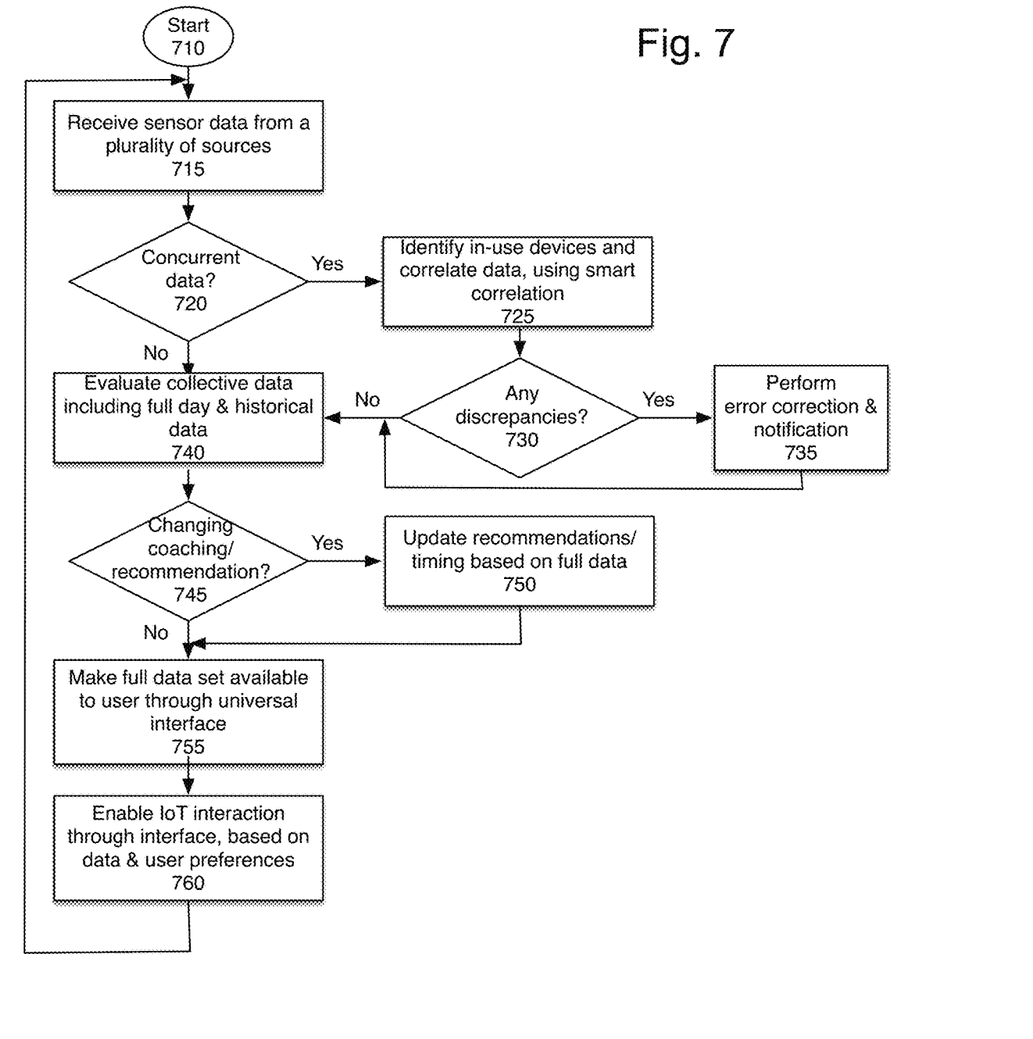
FIG. 7 is a flowchart of one embodiment of integration of sensor data from a plurality of sensors.

FIG. 7 is a flowchart of one embodiment of integration of sensor data from a plurality of sensors. The process starts at block 710. At block 715, the system receives sensor data from a plurality of sources. The plurality of sources may include the smart seating system, wearable devices, in-bed sleep monitoring devices, mobile devices with sensors, etc. In one embodiment, the system which receives and accumulates this data may be the user's mobile device. In one embodiment, the system may be a remote server to which each of these devices sends data. In one embodiment, the data is sent discontinuously, as each of the monitoring systems is set up.

At block 720, the process determines whether there is concurrent data. In one embodiment, all data has time associated with it. In one embodiment, time stamps based on network time on the user's mobile device. While this may not be completely accurate to the time determined by the official NIST US time, because the user's mobile device remains the same device, it is consistent among the multiple sensor systems. Concurrent data is data collected from multiple sensors with the same time indication. For example, a user wearing a wristband monitor and using smart seating may have data collected from both the wristband and the smart seating. However, the wristband may send the data continuously, while the smart seating may send bursts of data periodically, for example. Thus, the data set may be received at different times, and in different formats.

If there is concurrent data, at block 725 the in-use devices are identified, and the data is correlated. In one embodiment, this means the system as a preliminary matter determines whether the user is using the device. In this context, using means that the user is physically in contact with the device, whether by sitting on it (smart seating), laying on it (smart bed), wearing it (wearable devices), carrying it (mobile device), etc. Sometimes, a device may be providing data when the user is not actually engaged with it. For example, a user may have placed a wearable device in the cup holder of their vehicle, which means that motion is produced, but the device is not worn. Therefore, attempts to calculate heart rate or other data is not likely to be useful. Similarly, a smart seat may have had a briefcase or file placed on it, triggering sensors without the device being actually in use. In one embodiment, the micromotion characteristics of human bodies are used to validate that the device is currently in-use, rather than experiencing motion because of another trigger. If the system identifies one device as not being in actual use, its data is discarded, and the system determines that there is no concurrent data.

If the system identifies that both devices (or two or more devices) are in concurrent use, at block 730 the process determines whether there are discrepancies between the detected data sets. A discrepancy is defined as non-compatible data, e.g. one sensor is indicating something that cannot be reconciled with the data from the other sensor. If there are discrepancies, at block 735 error correction is performed. In one embodiment, this may involve indicating that the less consistent data source is indicating an error. In one embodiment, the user may be notified of such errors/discrepancies. In one embodiment, the user may be prompted to reboot or otherwise reset the device which appears to indicate an error. The process then continues to block 740. If there are no discrepancies, the process continues to block 740 directly.

At block 740, the collective data is evaluated. The evaluation utilizes the correlated data from multiple sensors, over time. In one embodiment, the use of historical data and historical analysis ensures that the system evaluates the data in the context of the real user, rather than an idealized "person."

At block 745, the process determines whether the coaching or recommendations should change, based on the data. If so, at block 750 the recommendations, coaching, and/or timing are updated based on the data analysis.

At block 755, the data set is made available through a universal interface. The universal interface in one embodiment presents the cumulative data, and enables the user to drill down to individual data sets and data sources. In one embodiment, the cumulative data is presented as a chart, indicating the user's health, sleep patterns, activity levels, and other relevant data.

At block 760, the IoT interaction is enabled through the interface, based on the data set and user preferences.

Figure 8:
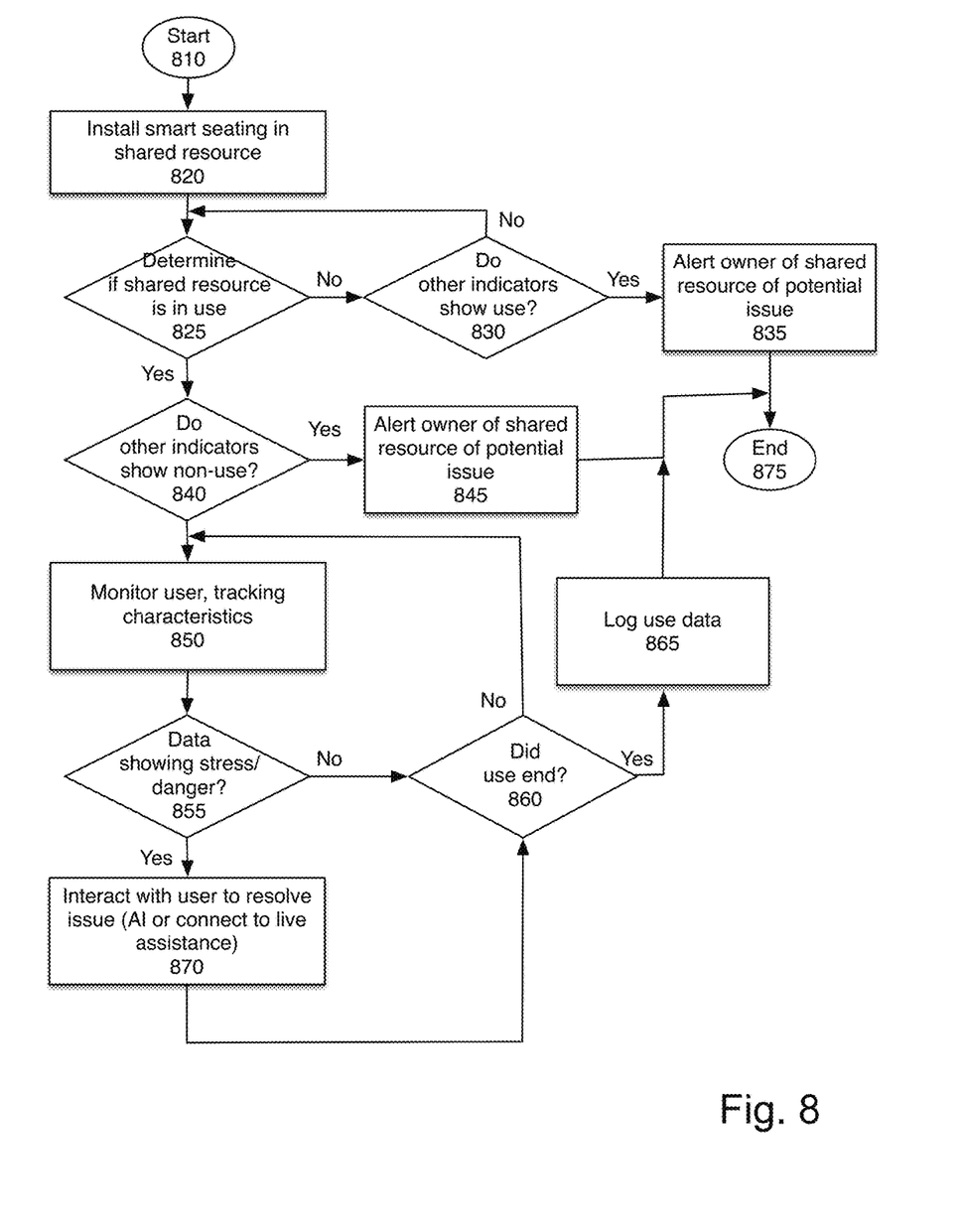
FIG. 8 is a flowchart of an exemplary use case for the smart seating system.

FIG. 8 is a flowchart of an exemplary use case for the smart seating system. An exemplary system may be a smart seating in a shared resource. A shared resource may for example by a conference room seat, or a seat in hotel lobby or the like. Another type of shared resource may be a vehicle such as an UBER™ service car, where the passenger seats, and/or the driver's seat, have a smart seat. This enables the monitoring of the states of the one or more people utilizing the smart seating. In one embodiment, in scenarios where there are other monitoring systems, for example the mobile application of UBER™ or the wireless system in a hotel, the smart seating may provide a validation of data from other sources.

The process starts at block 810. At block 820 the smart seat is installed in the shared resource. In one embodiment, the installation may include installing chairs including smart seats, or placing the seat cushions on existing seats.

At block 825, the smart seat data is used to determine if the shared resource is in use. As discussed above, the smart seating monitor's the user's physiological signals based on one or more sensors. This data is used to determine whether the resource is in use (e.g. whether there is a user sitting in the smart seat.)

If the determine is that there is no one in the seat, but other indicates show that the seat is in use, at block 830, the owner of the shared resource is alerted of a potential issue. In one embodiment, this may be an indicator of fraud (e.g. someone claiming to be in a meeting that they are not attending, or someone claiming to have a fare when that person is not in the vehicle.) It may also be that either the smart seat or the other indicators are malfunctioning. After the owner is alerted, the process ends at block 875. If the indicators also showed that the resource was not in use, the process returns to block 825 to continue monitoring the data from the smart seating.

If the smart seating indicates that the shared resource is in use, the process continues to block 840. At block 840, the process determines whether other indicates show non-use. Again, this may be because of fraud, malfunction, or a mis-indication. For example, a heavy suitcase or large dog may cause the smart seat to erroneously indicate that a smart seat is occupied, for a few seconds. Because the smart seating monitors the user's physiological signals, anything other than a person will be quickly identified. In one embodiment, to eliminate such erroneous indicators, the system obtains a set of measurements (in one embodiment one minute of measurements, in another embodiment at least 10 seconds of measurement) prior to making this determination. Again, if the indicators do not match, the owner is alerted, at block 845. The process then ends at block 875. In one embodiment, although the system indicates that the process ends, the system does continue to monitor data.

If there is no mismatch the process continues to block 850. At block 850, the user's data is monitored, and the user characteristics are tracked. In one embodiment, because the physiological signals are monitored, the system can sense when there is stress, or potential danger based on bodily reactions.

At block 855, the process determines whether the data shows stress. If so, at block 870, the user's issue is addressed. In one embodiment, the system may directly interact with the user, e.g., an artificial intelligence system may address the cause of the issue. In one embodiment, the system may connect the user to live assistance. In one embodiment, if the user is connected to live assistance, the person providing assistance is provided the relevant data from the smart seating and other sensors. For example, after a fender bender in a smart seating equipped car, the live assistance would be provided the location of the vehicle, the speed prior to impact, the size of the jolt, the stress level of the driver (if the driver's seat is equipped) and/or the stress level of the passenger(s) if that is equipped. This data should enable the system to provide relevant, prompt, and useful assistance. Of course, similarly if there is violence or other negative interactions, they may be identified and addressed by the system.

The process then continues to block 860. At block 860 the process determines whether the use ended. If the use has not yet ended, the process returns to block 850 to continue monitoring the user. If the use has ended, e.g. the user has left the smart seating, the process continues to block 865.

At block 865, the use data is logged. In one embodiment, the user's personal data may be made available to the user, via an application. This may enable the user to obtain data about, for example, movement and stress in meetings or in vehicles. As noted above, this may also be integrated into the user's integrated health system.

The logging also provides log data to the owner of the shared resource. In one embodiment, in a car-service, such as Uber, the owner may be the owner of the service rather than the vehicle owner. In one embodiment, the log may also be used in a cumulative data set. This enables, for example, the prediction of which rides are highly stressful, or where accidents happen. Additionally, in one embodiment, the data, or a processed subset of it, may be associated with the user's profile. The process then ends at block 875.

Figure 9:
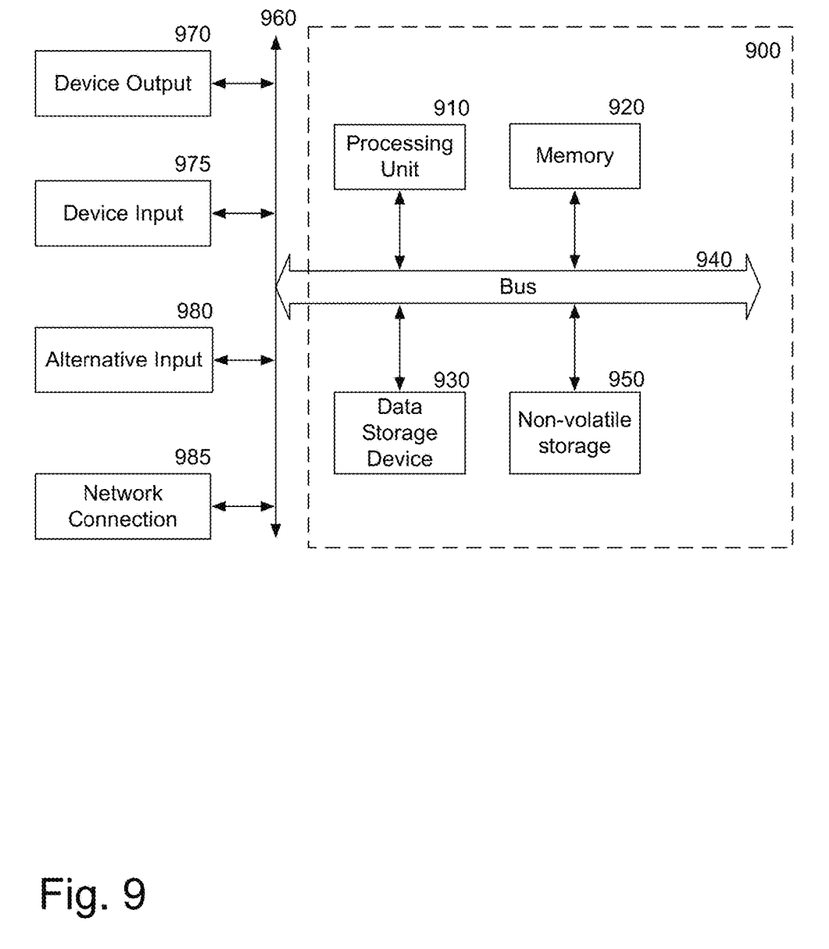
FIG. 9 is a block diagram of one embodiment of a computer system.

FIG. 9 is a block diagram of one embodiment of a computer system. As discussed above, various elements of the described computer system may be used in the special purpose smart seating system described. Similarly, the mobile device which may be used with the smart seating system may include one or more elements of the described computer system.

The data processing system illustrated in FIG. 9 includes a bus or other internal communication means 940 for communicating information, and a processing unit 910 coupled to the bus 940 for processing information. The processing unit 910 may be a central processing unit (CPU), a digital signal processor (DSP), or another type of processing unit 910.

The system further includes, in one embodiment, a random-access memory (RAM) or other volatile storage device 920 (referred to as memory), coupled to bus 940 for storing information and instructions to be executed by processor 910. Main memory 920 may also be used for storing temporary variables or other intermediate information during execution of instructions by processing unit 910.

The system also comprises in one embodiment a read only memory (ROM) 950 and/or static storage device 950 coupled to bus 940 for storing static information and instructions for processor 910. In one embodiment, the system also includes a data storage device 930 such as a magnetic disk or optical disk and its corresponding disk drive, or Flash memory or other storage which is capable of storing data when no power is supplied to the system. Data storage device 930 in one embodiment is coupled to bus 940 for storing information and instructions.

The system may further be coupled to an output device 970, such as a cathode ray tube (CRT) or a liquid crystal display (LCD) coupled to bus 940 through bus 960 for outputting information. The output device 970 may be a visual output device, an audio output device, and/or tactile output device (e.g. vibrations, etc.)

An input device 975 may be coupled to the bus 960. The input device 975 may be an alphanumeric input device, such as a keyboard including alphanumeric and other keys, for enabling a user to communicate information and command selections to processing unit 910. An additional user input device 980 may further be included. One such user input device 980 is cursor control device 980, such as a mouse, a trackball, stylus, cursor direction keys, or touch screen, may be coupled to bus 940 through bus 960 for communicating direction information and command selections to processing unit 910, and for controlling movement on display device 970.

Another device, which may optionally be coupled to computer system 900, is a network device 985 for accessing other nodes of a distributed system via a network. The communication device 985 may include any of a number of commercially available networking peripheral devices such as those used for coupling to an Ethernet, token ring, Internet, or wide area network, personal area network, wireless network or other method of accessing other devices. The communication device 985 may further be a null-modem connection, or any other mechanism that provides connectivity between the computer system 900 and the outside world.

It will be appreciated by those of ordinary skill in the art that the particular machine that embodies the present invention may be configured in various ways according to the particular implementation. The control logic or software implementing the present invention can be stored in main memory 920, mass storage device 930, or other storage medium locally or remotely accessible to processor 910.

It will be apparent to those of ordinary skill in the art that the system, method, and process described herein can be implemented as software stored in main memory 920 or read only memory 950 and executed by processor 910. This control logic or software may also be resident on an article of manufacture comprising a computer readable medium having computer readable program code embodied therein and being readable by the mass storage device 930 and for causing the processor 910 to operate in accordance with the methods and teachings herein.

The present invention may also be embodied in a handheld or portable device containing a subset of the computer hardware components described above. For example, the handheld device may be configured to contain only the bus 940, the processor 910, and memory 950 and/or 920.

The handheld device may be configured to include a set of buttons or input signaling components with which a user may select from a set of available options. These could be considered input device #1 975 or input device #2 980. The handheld device may also be configured to include an output device 970 such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose appliance including a subset of the computer hardware components described above, such as a kiosk or a vehicle. For example, the appliance may include a processing unit 910, a data storage device 930, a bus 940, and memory 920, and no input/output mechanisms, or only rudimentary communications mechanisms, such as a small touch-screen that permits the user to communicate in a basic manner with the device. In general, the more special-purpose the device is, the fewer of the elements need be present for the device to function. In some devices, communications with the user may be through a touch-based screen, or similar mechanism. In one embodiment, the device may not provide any direct input/output signals, but may be configured and accessed through a website or other network-based connection through network device 985.

It will be appreciated by those of ordinary skill in the art that any configuration of the particular machine implemented as the computer system may be used according to the particular implementation. The control logic or software implementing the present invention can be stored on any machine-readable medium locally or remotely accessible to processor 910. A machine-readable medium includes any mechanism for storing information in a form readable by a machine (e.g. a computer). For example, a machine-readable medium includes read-only memory (ROM), random access memory (RAM), magnetic disk storage media, optical storage media, flash memory devices, or other storage media which may be used for temporary or permanent data storage. In one embodiment, the control logic may be implemented as transmittable data, such as electrical, optical, acoustical or other forms of propagated signals (e.g. carrier waves, infrared signals, digital signals, etc.).

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

We claim:

1. A smart seating system comprising:
    smart seating comprising:
        a proximity sensor to detect a user's proximity to the smart seating;
        a motion sensor in a seating area to collect user motion data about a user when the user is seated, the motion sensor activated based on data from the proximity sensor;
        a memory to store user data comprising proximity data and the user motion data;
        an analytics processor to validate the user data with external user data from an external sensor not part of the smart seating, to confirm a presence of the user on the smart seating;
        when the user presence is confirmed, a stress analyzer to determine a stress level of a user, based on the user motion data, and to prompt the user by user interface to take a stress break when the stress level is above a threshold; and
        the user interface further to provide coaching for stress reduction when the stress level is above the threshold; and
        the analytics processor to implement repetitive motion detection, to detect the user executing a repetitive motion based on the user motion data, and to prompt the user to take a break from the repetitive motion.

2. The smart seating system of claim 1, wherein the smart seating is implemented in one of: an office chair, a car seat, a seat cushion, a sensor pad, and a seat and back cushion.

3. The smart seating system of claim 1, wherein the smart seating further comprises:
    clocks and timers; and
    an alert logic to alert the user of a time to take a break.

4. The smart seating system of claim 1, further comprising:
    an inactivity detector to detect the user being inactive over a time, and to prompt the user to get up and stretch.

5. The smart seating system of claim 1, wherein the stress break comprises one of: meditation, breathing exercises, and focus.

6. The smart seating system of claim 1, further comprising:
    a coach to provide the coaching, the coaching comprising one or more of: stretches, meditation, breathing exercises, walking, taking a break from a computer.

7. The smart seating system of claim 1, further comprising:
    environmental sensors to detect environmental conditions.

8. The smart seating system of claim 1, further comprising:
    an extractor to identify a heart rate and a respiration of the user based on the user data; and
    the analytics processor to utilize the heart rate and the respiration data to identify stress.

9. The smart seating system of claim 1, further comprising:
    data integration to integrate data from a plurality of sensors in addition to the smart seating.

10. A smart seating system comprising:
    smart seating comprising:
        a proximity sensor to detect a user's proximity to the smart seating;

a motion sensor to detect user motion on the smart seating, the motion sensor activated based on data from the proximity sensor, the motion sensor to obtain user motion data;

a memory to store user data comprising proximity data and the user motion data a communication logic to transmit the user data;

an analytics processor system to receive the user data from the communication logic, the analytics processor system comprising:

a processor to validate the user data with external user motion data, from an external sensor not part of the smart seating, and to confirm a presence of a user on the smart seating;

when the user's presence is confirmed, the analytics processor further to analyze the user motion data and implement a stress analyzer to determine a stress level of a user, based on the user motion data;

a user interface to provide coaching for stress reduction, when the determined stress level of the user is above a threshold;

the processor to implement repetitive motion detection to detect the user executing a repetitive motion based on the user motion data, and to prompt the user to take a break from the repetitive motion.

11. The smart seating system of claim 10, wherein the smart seating is implemented in one of: an office chair, a car seat, a seat cushion, a sensor pad, and a seat and back cushion.

12. The smart seating system of claim 10, wherein the smart seating further comprises:

clocks and timers; and an alert logic to alert the user of a time to take a break.

13. The smart seating system of claim 10, further comprising:

an inactivity detector to detect the user being inactive over a time, and to prompt the user to get up and stretch.

14. The smart seating system of claim 10, further comprising:

a repetitive motion detector to detect the user executing a repetitive motion, and to prompt the user to take a break from the repetitive motion.

15. The smart seating system of claim 10, further comprising:

the user interface to present a coach to provide the coaching, the coaching comprising one or more of: stretches, meditation, breathing exercises, walking, taking a break from a computer.

16. The smart seating system of claim 10, further comprising:

environmental sensors to detect environmental conditions.

17. The smart seating system of claim 10, further comprising:

an extractor to identify a heart rate and a respiration of the user based on the data; and the analytics processor to utilize the heart rate and the respiration data to identify stress.

18. The smart seating system of claim 10, further comprising:

data integration to integrate data from a plurality of sensors in addition to the smart seating.

19. A smart seating system comprising:

smart seating comprising:

a proximity sensor to detect a user's proximity to the smart seating;

a motion sensor to detect user motion on the smart seating, and obtain user motion data;

a memory to store user data comprising proximity data and the user motion data;

a communication logic to transmit the user data;

an analytics processor system to receive the user data from the communication logic, the analytics processor system comprising:

an analytics processor to validate the user data with external user motion data, from an external source sensor not part of the smart seating, and to confirm a presence of the user on the smart seating;

when the user's presence is confirmed, the analytics processor further to analyze the user motion data and implement a stress analyzer to determine a stress level of a user, based on the user motion data;

a response system to interact with a user when the determined stress level is above a threshold, the response system including a user interface to provide coaching to the user to reduce the stress level; and the analytics processor to implement repetitive motion detection, to detect the user executing a repetitive motion based on the user motion data, and to prompt the user to take a break from the repetitive motion.

20. The smart seating system of claim 19, wherein the smart seating is implemented in an office chair, designed for use in a work environment.

* * * * *